United States Patent [19]

Briggs et al.

[11] Patent Number: 5,323,780
[45] Date of Patent: Jun. 28, 1994

[54] ARTIFACT-FREE IMAGING CONTRAST AGENT

[75] Inventors: Richard W. Briggs, Gainesville, Fla.; Thomas Liebig, Bremen, Fed. Rep. of Germany; Pablo R. Ros; J. Ray Ballinger, both of Gainesville, Fla.

[73] Assignee: University of Florida Research Foundation, Inc., Gainesville, Fla.

[21] Appl. No.: 925,549

[22] Filed: Aug. 7, 1992

[51] Int. Cl.$^5$ .............................................. A61B 5/05
[52] U.S. Cl. .................................. 128/653.4; 128/898; 128/653.1; 424/9
[58] Field of Search ................... 128/653.1, 653.4, 654, 128/659, 898, 899; 604/19, 20; 600/1–4; 424/646–648, 9; 436/173

[56] References Cited

U.S. PATENT DOCUMENTS

| | | | |
|---|---|---|---|
| 4,926,124 | 5/1990 | Le Roux | 128/653.2 |
| 4,962,763 | 10/1990 | Sato et al. | 128/653.2 |
| 5,023,072 | 6/1991 | Cheng | 128/653.4 |
| 5,128,121 | 7/1992 | Berg et al. | 128/653.4 |

OTHER PUBLICATIONS

Hahn et al, *Radiology*, vol. 164, "Ferrite Particles for Bowel Contrast in MR Imaging: Design Issues and Feasibility Studies," p. 37 (1987).
Hahn et al, *Radiology*, vol. 175, "First Clinical Trial of a New Superparamagnetic Iron Oxide for Use as an Oral Gastrointestinal Contrast Agent in MR Imaging," p. 695 (1990).
Hahn et al, *Magn. Reson. Imaging*, vol. 6, Suppl. 1, "Image Artifacts Introduced by MRI Gastrointestinal Contrast Agents: Magnitude, Cause and Amelioration," p. 78 (1988) [6th SMRI, abstract 250].
Rubin et al, *Radiology*, vol. 181 (P), "Magnetic Susceptibility Artifacts with Superparamagnetic Gastrointestinal Contrast Media: Importance of Optimizing Formulation," p. 93 (1991) [77th RSNA, abstract 29].
Tilcock et al., *J. Magn. Reson. Imaging*, vol. 1, "Polymeric Gastrointestinal MR Contrast Agents," p. 463 (1991).
Wehrli et al, 10th Ann. SMRM Book of Abstracts, vol. 1, "A Novel Approach toward Measurement of the Diamagnetic Susceptibility of Bone," p. 250 (1991).
Cho et al, *Magn. Reson. Med.*, vol. 23, "Reduction of Susceptibility Artifact in Gradient-Echo Imaging," p. 193 (1992).
Young et al, *Magn. Reson. Imaging*, vol. 6, "The Benefits of Increasing Spatial Resolution as a Means of Reducing Artifacts Due to Field Inhomogeneities," p. 585 (1988).
Frahm et al., *Magn. Reson. Med.*, vol. 6, "Direct Flash MR Imaging of Magnetic Field Inhomogeneities by Gradient Compensation," p. 474 (1988).
Patz et al, *Magn. Reson. Med.*, vol. 10, "Missing Pulse Steady-State Free Precession," p. 194 (1989).
Mammone et al, *J. Magn. Reson. Imaging*, vol. 2 (P), "Clay/Paramagnetic Hybrid: A Biphasic Oral Contrast Agent over a Wide Range of Dilutions," p. 115 (1992) [abstract 280].
Liebig et al, 11th SMRM (Society of Magnetic Resonance in Medicine) Meeting, "An Artifact Free Luminal Contrast Agent for Gastrointestinal MRI," p. 1433 (Aug. 8–14, 1992) Berlin, Germany [work in progress].
Young et al. "Benefits of Increasing Spatial Resolution" *Magnetic Resonance Imaging*, vol. 6 pp. 585–590 (1988).

*Primary Examiner*—C. Fred Rosenbaum
*Assistant Examiner*—Chalin Smith
*Attorney, Agent, or Firm*—Kerkam, Stowell, Kondracki & Clarke

[57] ABSTRACT

A contrast agent useful for imaging a sample comprising a suspension in a medium acceptable for imaging (a) particles of a contrast agent possessing paramagnetic characteristics and (b) particles of a contrast agent possessing diamagnetic characteristics. Also disclosed is a method of imaging a sample which comprises introducing into the sample the above-described contrast agent and generating a substantially artifact-free image thereof. The combination of diamagnetic barium sulfate and superparamagnetic iron oxide (SPIO) in one suspension produces a macroscopic cancellation of positive and negative magnetic susceptibility components which eliminates susceptibility artifacts even with gradient echo pulse sequences. The relaxation properties which make the SPIO suspension a useful negative contrast agent are retained.

12 Claims, 4 Drawing Sheets

ARTIFACT-FREE IMAGING CONTRAST AGENT

BACKGROUND OF THE INVENTION

Research leading to the completion of the invention was supported, in part, by IRB Grant No. 70-91 provided by Advanced Magnetics, Inc. of Cambridge, Mass., and IRB Grant No. 457-90 provided by E-Z-EM, Inc. of Westbury, N.Y.

1. Field of the Invention

The present invention relates to imaging contrast agents, in particular, NMR imaging contrast agents.

2. Discussion of the Prior Art

It is well known to enhance NMR (nuclear magnetic resonance) images by, prior to conducting the imaging, introducing into the sample to be imaged ferromagnetic, diamagnetic or paramagnetic particles which shadow the image produced to intensify and contrast the image generate by the NMR sensitive nuclei. See, for example, the disclosures of U.S. Pat. Nos. 4,731,239; 4,863,715; 4,749,560; 5,069,216; 5,055,288; 5,023,072; 4,951,675; 4,827,945 and 4,770,183, the entire contents and disclosures of all of which are incorporated herein by reference.

A disadvantage associated with the use of NMR image contrast agents, however, resides in the fact that the internal magnetic properties of the various contrast agents employed heretofore affect the applied external field during the imaging process. These interactions of the paramagnetic or diamagnetic properties of the contrast agents with the applied external magnetic field give rise to irregularities in the resulting image, commonly referred to as imaging artifacts.

The application of magnetic resonance imaging (MRI) to abdominal imaging is potentially revolutionary, but currently is seriously limited by the inability to distinguish tumors, abscesses and other abnormalities from normal structures, e.g., bowel. As for computed tomography, the use of oral or rectal contrast agents is expected to dramatically improve the diagnostic value of MRI for abdominal diseases. Currently, superparamagnetic iron oxide (SPIO) is the best oral contrast agent available for use in MRI.

Iron oxide acts as a gastrointestinal (GI) MRI contrast agent primarily due to the dipolar interaction of the unpaired electrons of iron with the water protons in the body. In addition, its internal magnetization aligns parallel to an applied external field, increasing the magnetic field strength nearby. This is known as positive magnetic susceptibility, and also leads to large field gradients near the articles. Both of these mechanisms cause loss of signal intensity within the bowel. This loss of signal causes the desired enhancement of the difference in the appearance of bowel and other normal and abnormal structures in magnetic resonance images.

A problem with SPIO suspensions in the past has been that they not only affect the volume that actually contains the suspension (i.e., bowel), but also lead to artifactual signal loss in the region surrounding this area. This phenomenon is called susceptibility artifact and is more pronounced with greater field strength and with gradient recalled echo pulse sequences. This artifact reduces the diagnostic usefulness of SPIO, especially for gradient echo sequences which otherwise have many advantages for MRI of the abdomen.

Barium sulfate suspensions are also used as oral contrast agents for GI MRI. Barium sulfate is a diamagnetic substance; its paired electrons interact with an external magnetic field to produce internal magnetization oriented opposite to the applied field. This is known as negative magnetic susceptibility, and also produces loss of signal intensity due to diffusion of water molecules through the field gradients around the particles.

It is an object of the present invention to provide imaging contrast agents which do not suffer from the above-noted disadvantages and a method of imaging which produces an image substantially artifact-free.

(a) $T_1$-weighted image, TR=300 ms, TE=20 ms (b) "proton density" image, TR=1800 ms, TE=30 ms (c) $T_2$-weighted image, TR=1800 ms, TE=90 ms (d) gradient-recalled echo image, TR=100 ms, TE=40 ms, 30° flip angle (e) gradient-recalled echo image, TR=100 ms, TE=40 ms, 30° flip angle.

Sample suspensions in 2.5% w/v aqueous vehicle are, top to bottom in FIGS. 3a-3d:

(1) Fe100: $Fe_3O_4$, 175 mg Fe/liter (2) Fe75/Ba25: $Fe_3O_4$, 131.25 mg Fe/liter, and $BaSO_4$, 150% w/v (3) Fe50/Ba50: $Fe_3O_4$, 87.5 mg Fe/liter, and $BaSO_4$, 100% w/v (4) Fe25/Ba75: $Fe_3O_4$, 43.75 mg Fe/liter, and $BaSO_4$, 50% w/v (5) Ba100: $BaSO_4$, 200% w/v.

Figure 3C:
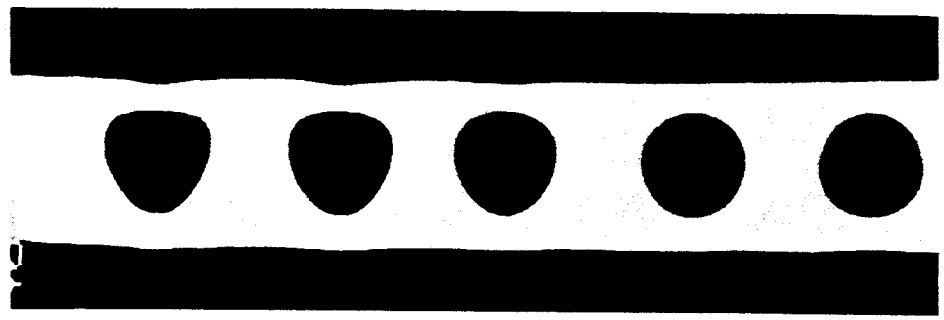
FIGS. 3a-3e show proton MR images of the contrast agent suspensions.
Figure 3B:
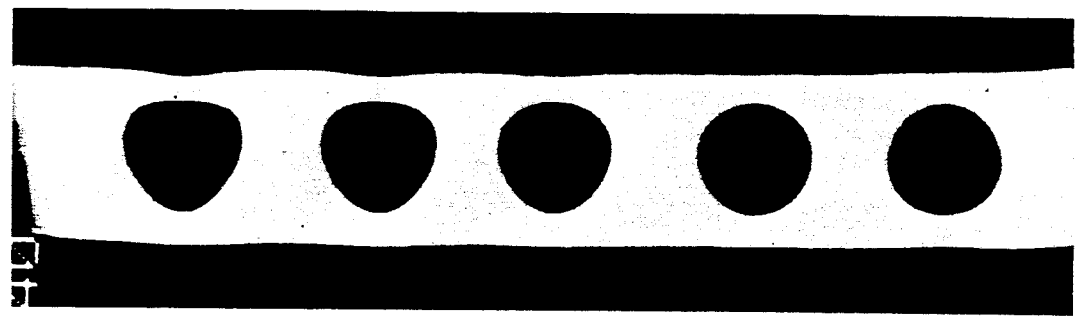
Figure 3A:
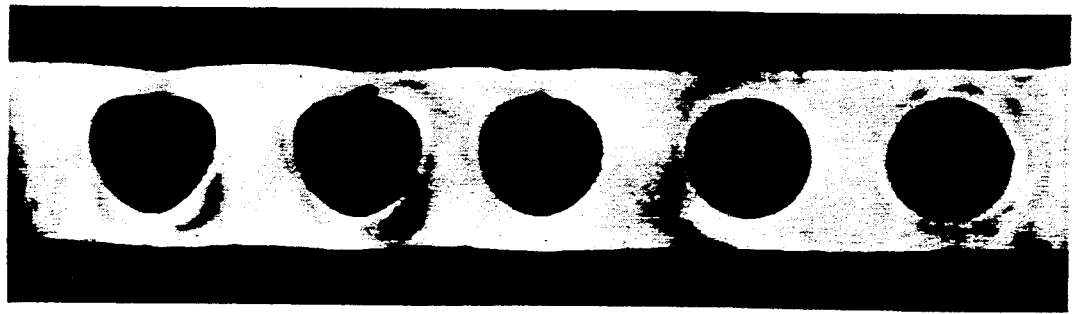
Figure 3D:
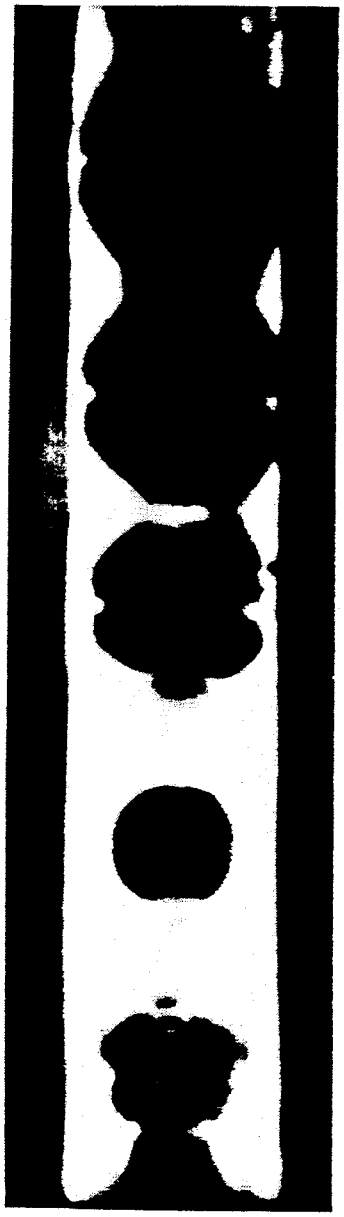
Figure 3E:
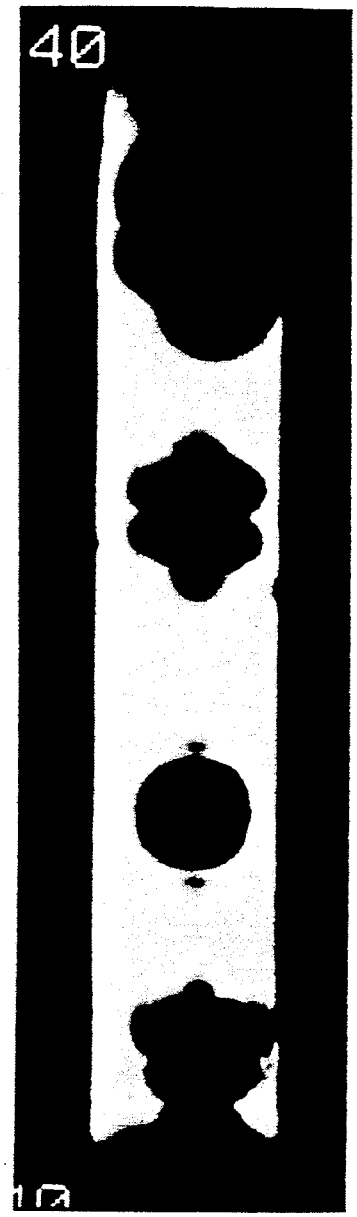

For FIG. 3e, sample suspensions in 2.5% w/v aqueous vehicle are, top to bottom:

(1) Fe100: $Fe_3O_4$, 175 mg Fe/liter (2) Fe25: $Fe_3O_4$, 43.75 mg Fe/liter (3) Fe25/Ba75: $Fe_3O_4$, 43.75 mg Fe/liter, and $BaSO_4$, 50% w/v (4) Ba100: $BaSO_4$, 200% w/v.

Figure 4:
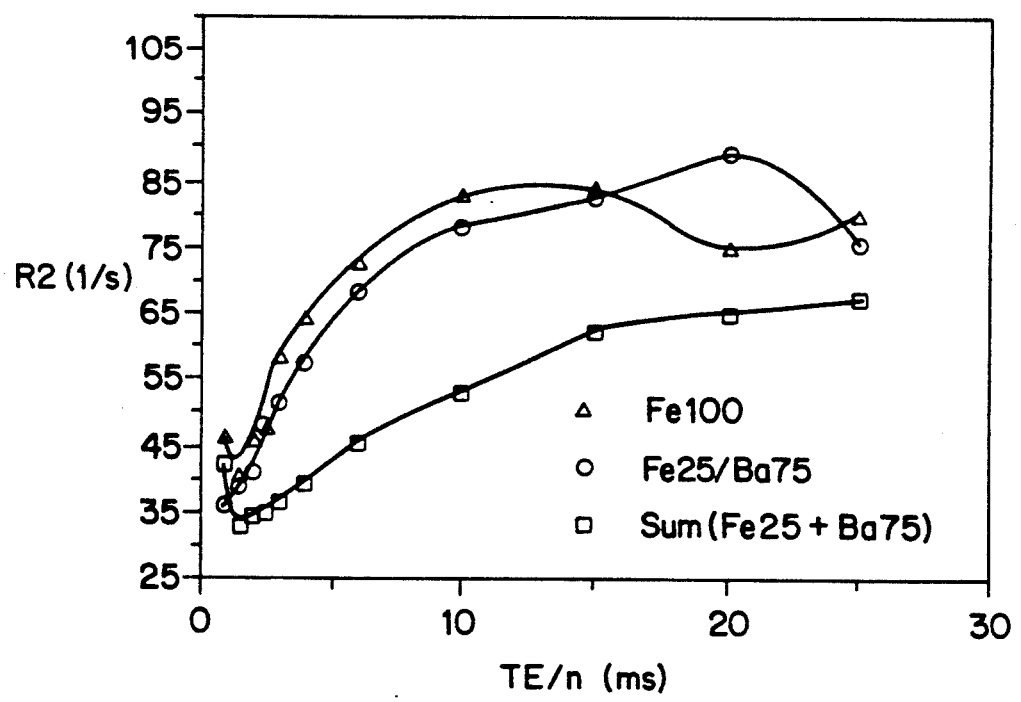

FIG. 4 shows transverse relaxation rates $R_2$ as a function of the echo spacing TE/n ($=2\tau$) for the Fe100 and Fe25/Ba75 suspensions, as well as the sum of the rates for the Fe25 and Ba75 suspensions. Points represent the mean of 3-5 individual determinations. To preserve clarity of presentation, error bars are not shown; the mean standard deviation expressed as percent of the mean is 14.5%±5.7%.

SUMMARY OF THE INVENTION

The above and other objects are realized by the present invention, one embodiment of which is a contrast agent useful for imaging a sample comprising a suspension in a medium acceptable for imaging (a) particles of a contrast agent possessing paramagnetic characteristics and (b) particles of a contrast agent possessing diamagnetic characteristics.

Another embodiment of the invention relates to a method of imaging a sample which comprises introducing into the sample the above-described contrast agent and generating a substantially artifact-free image thereof.

DETAILED DESCRIPTION OF THE INVENTION

It will be understood by those skilled in the art that for purposes of describing the present invention, the terms discussed hereinbelow have the following meanings and definitions.

The term "paramagnetic" as used herein is intended to include those substances described as "ferromagnetic" and "superparamagnetic" as well as paramagnetic, all of which have positive magnetic susceptibility characteristics.

The phrase " . . . the positive magnetic susceptibility . . . offsets the negative magnetic susceptibility . . . to produce . . . a substantially zero magnetic susceptibility . . . " is intended to mean the respective positive and negative magnetic susceptibilities are matched so as to produce a contrast agent which results in an artifact-free image. This "matching" may not necessarily produce a zero magnetic susceptibility since the suspending medium and any other components present in the suspension may have an inherent magnetic susceptibility which must be taken into account when balancing the amounts of paramagnetic and diamagnetic particles to produce a contrast agent which yields an artifact-free image upon imaging.

Any suitable diamagnetic material possessing negative magnetic susceptibility characteristics may be employed in the practice of the invention. Barium sulfate, preferably in the form of a mixture of barites and substantially pure barium sulfate, is exemplary of suitable diamagnetic substances.

Any suitable paramagnetic material, e.g., iron oxide (ferrite), possessing positive magnetic susceptibility characteristics may be employed in the practice of the invention. Particularly preferred is superparamagnetic iron oxide (SPIO).

Any suitable suspending medium may be employed for preparing suspensions of the respective paramagnetic and diamagnetic particles, as well as the mixture thereof. For example, an aqueous solution of vegetable gums (e.g., 2.35% w/v) may be employed to prepare a suspension of barium sulfate. Water may be used to prepare the suspension of SPIO. Those skilled in the art are well aware of suitable media for use in preparing image contrasting agents. It is preferred, of course, when the agent is to be employed in NMR imaging of a patient (human or non-human) that the medium comprise a physiologically acceptable one.

Amounts of the respective paramagnetic and diamagnetic particles are employed so as to produce a mixture, the use of which as a contrasting agent yields an artifact-free image.

An example of such a suspension is one comprising a mixture of (1) a 25% v/v suspension of SPIO in water (175 mg/liter) and (2) a 75% v/v suspension of a mixture of 56.8% by weight of Barytes #1 and 43.2% by weight of USP $BaSO_4$ in a 2.35% w/v aqueous solution (220% w/v=80% w/w). This suspension, when employed as an imaging contrasting agent in an NMR imaging method, produces good contrast in all pulse sequences with no artifactual images.

The combination of materials with positive and negative magnetic susceptibilities in a suspension results in increased field gradients between suspended particles with improved relaxivity on a microscopic scale. On a macroscopic scale, mixing the two suspensions (one with positive and one with negative magnetic susceptibility) in the correct proportions produces a suspension with zero bulk susceptibility and no artifacts.

Figure 1:
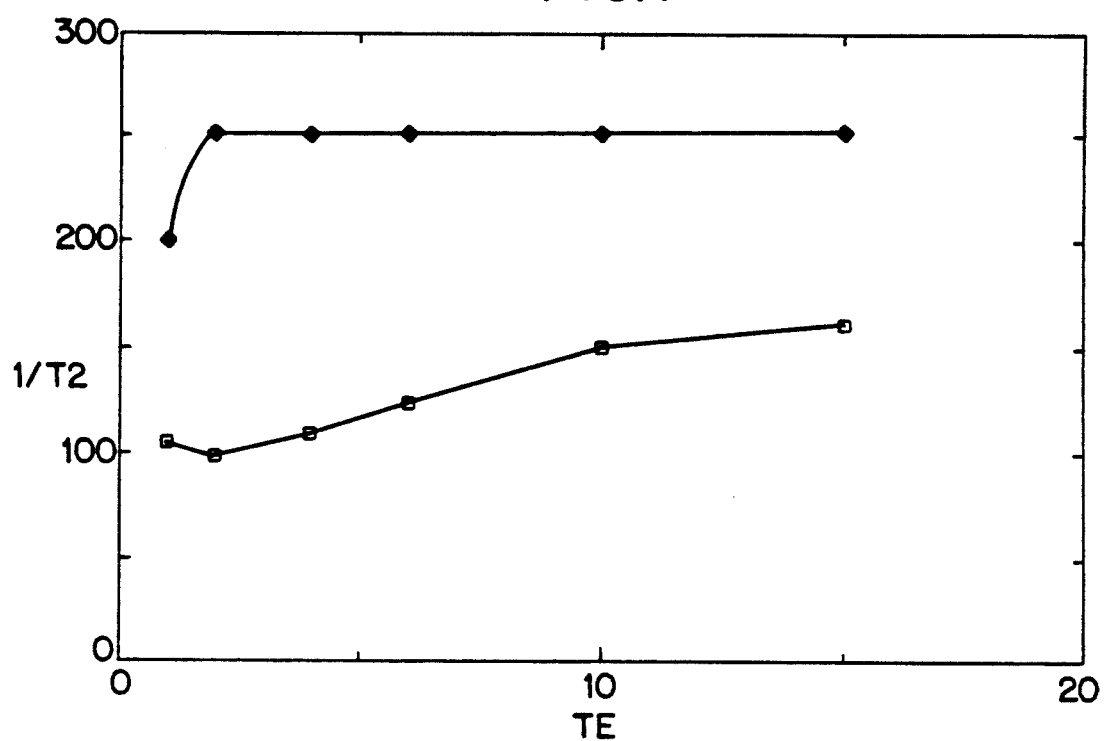
FIG. 1 is a graphical depiction comparing the relaxivities of contrast agents comprising (a) mixture of ferrite and barium sulfate and (b) ferrite alone.
Figure 2:
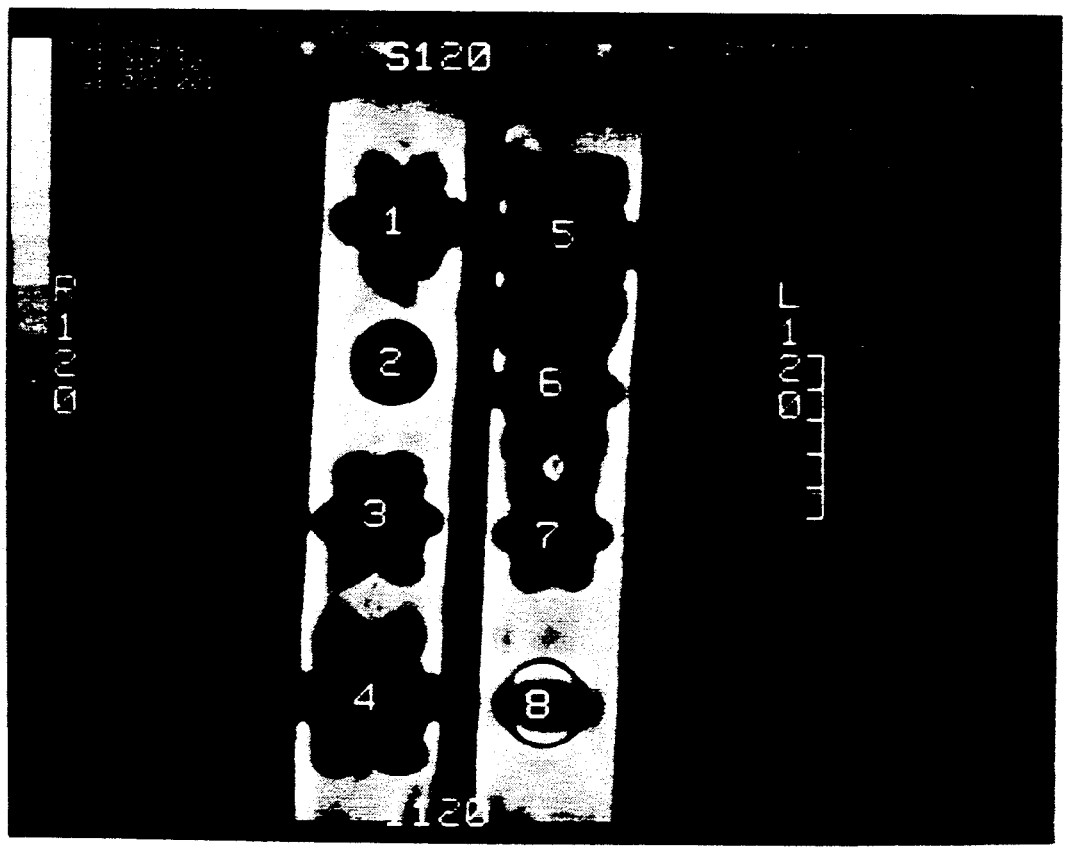
FIG. 2 depicts the magnetic susceptibility artifacts produced by various suspensions of barium sulfate and ferrite.

It has been found that a combination of 25% v/v SPIO (175 mg/liter) and 75% v/v barium sulfate suspension (220% w/v) shows no artifact and produces good contrast in all pulse sequences. FIG. 1 graphically demonstrates the improved relaxivity of a 50% v/v AMI 121/50% v/v Liquid HD suspension over the sum of the relaxivities of each of its components. FIG. 2 demonstrates the magnetic susceptibility artifacts produced by different suspensions of barium sulfate and ferrite in a gradient echo pulse sequence. Note that suspension 2 does not produce any artifact. In FIG. 2, 1 = pure Liquid HD
2 = 25% SPIO/75% Liquid HD
3 = 50% SPIO/50% Liquid HD
4 = 75% SPIO/25% Liquid HD
5 = pure SPIO suspension
6 = 50% SPIO/50% water
7 = 25% SPIO/75% water
8 = pure water.

EXAMPLE

Powdered $Fe_3O_4$ (a Fe(III)/Fe(II) mixture) was obtained from Alfa/Johnson Matthey. The $Fe_3O_4$ particle size was 0.3–0.4 $\mu$m. The vehicle used for particle suspension and $BaSO_4$ (particle size 3 $\mu$m) were obtained from E-Z-EM, Inc. The $BaSO_4$ and $Fe_3O_4$ were mixed dry as powders with the vehicle and then diluted with water [Tilcock et al, *J. Magn. Reson. Imaging*, vol. 1, page 463 (1991) ]. Final stock concentrations were 200% $BaSO_4$ (Ba100), 175 mg Fe/liter $Fe_3O_4$ (Fe100), and 2.5% w/v vehicle. The $Fe_3O_4$ suspension was mixed with the $BaSO_4$ suspension in 1:3 (Fe25/Ba75), 1:1 (Fe50/Ba50), and 3:1 (Fe75/Ba25) volume ratios; a 1:3 dilution of the $Fe_3O_4$ suspension (Fe25) and a 3:1 dilution of the $BaSO_4$ suspension (Ba75) were made with 2.5% w/v vehicle solution to yield a 43.75 mg Fe/liter $Fe_3O_4$ suspension and a 150% w/v $BaSO_4$ suspension. The samples (20 mL) were placed in 2.5 cm diameter glass bottles in a water bath phantom.

Images were obtained at 1.5 T (GE Signa) with a quadrature head coil using $T_1$-weighted (TR=300 ms, TE=20 ms, 1 NEX, 256×128 matrix, 28 cm FOV, 5 mm slice) and $T_2$-weighted (TR=1800 ms, TE=30/90 ms, 1 NEX, 256×128 matrix, 28 cm FOV, 5 mm slice) spin echo and GRASS gradient echo (TR=100 ms, TE=30, 40, 60 ms; TR=80 ms, TE=40 ms; TR=50 ms, TE=25 ms; 30° flip angle; 4 NEX; 256×128 matrix; 28 cm FOV; 5 mm slice) sequences.

For measurement of $T_1$ and $T_2$ relaxation times, a 2T SISCO (Spectroscopy Imaging Systems Corp.) system was used. Calculations were performed with the VNMR software on a Sun SPARC 2/GX workstation. The inversion recovery pulse sequence with TR=10–15 s ($\geq 5T_1$) and TI ranging from 0.01 s to 13 s (10–12 values per measurement) was used for $T_1$ determination. A multiple echo Carr-Purcell-Meiboom-Gill (CPMG) pulse sequence with TR=6–13 s ($\geq 5T_1$) and $2\tau$=1, 1.5, 2, 2.5, 3, 4, 6, 10, 15, 25, 35 ms (TE=$2\tau$n, where n is the number of echoes and $2\tau$ is the echo spacing) was used for $T_2$ measurements. The number of echoes was varied for each value of the echo spacing $2\tau$ (=TE/n) of the CPMG sequence to generate the transverse magnetization decay curve from which $T_2$ was calculated. In order to characterize the effect of diffusion on the signal decay, the relaxation rate (=$1/T_2$) as a function of $2\tau$, $R_2(2\tau)$, was plotted versus TE/n ($=2\tau$)

FIG. 3 shows images of the phantoms obtained at 1.5 Tesla with different imaging sequences. FIG. 3a is a $T_1$-weighted image (TR=300 ms, TE=20 ms), FIG. 3b is a "proton density" image (TR=1800 ms, TE=30 ms), FIG. 3c is a $T_2$-weighted image (TR=1800 ms, TE=90 ms), and FIG. 3d is a gradient-recalled echo image (TR=100 ms, TE=40 ms, 30° flip angle). Suspensions containing $Fe_3O_4$ appeared very dark and suspensions containing $BaSO_4$ appeared dark on "proton density" and $T_1$- and $T_2$-weighted images. All suspensions appeared dark in gradient echo images. These results are indicative of short $T_2$ for $BaSO_4$ and very short $T_2$ for $Fe_3O_4$. On gradient echo images, concentrated $BaSO_4$ suspensions produced some artifacts and $Fe_3O_4$ suspensions produced extensive artifacts. The 1:3 $Fe_3O_4$:$BaSO_4$ (Fe25/Ba75) mixture, however, produced no artifact. This was not due to dilution effects, as individual suspensions of $Fe_3O_4$ (Fe25, FIG. 3e) and $BaSO_4$ (Ba75) at the concentrations found in the 1:3 mixture did produce artifacts.

To better characterize the relaxation properties of the suspensions, $T_1$ and $T_2$ measurements were made at 2.0 Tesla. Table 1 shows the results of the $T_1$ experiments. The $T_1$ of the Fe100 sample is 1.17 s, those of the Fe25 and Ba75 samples are about twice as long, and that of the Fe25/Ba75 sample is intermediate between that of the Fe100 sample and those of the Fe25 and Ba75 samples. The $T_1$ obtained by summing the rates of the Fe25 and Ba75 samples is the same as that of the Fe100 sample. FIG. 4 shows the transverse relaxation rates $R_2$ as a function of the echo spacing TE/n ($=2\tau$) for the Fe100 and Fe25/Ba75 suspensions, as well as the sum of the rates of the Fe25 and Ba75 suspensions. The $R_2$ values for the Fe100 sample are slightly, but not significantly, greater than those of the Fe25/Ba75 sample. The $R_2$ values for the Fe100 and Fe25/Ba75 samples are greater than those obtained by summing the rates of the Fe25 and Ba75 suspensions, except for short echo times (TE/n <2 ms), where all the rates converge to similar values. All the suspensions have a significant contribution to $R_2$ from diffusion of water through field gradients around the suspended particles, as exhibited by the increase in $R_2$ with increasing echo spacing.

Water is diamagnetic with a negative susceptibility ($\chi = -13 \times 10^{-6}$ cgs units). Barium sulfate is even more diamagnetic ($\chi = -71.3 \times 10^{-6}$ cgs units). Iron oxide is paramagnetic with a strongly positive magnetic susceptibility. If suspensions of particles with opposing susceptibilities are mixed in the proper proportions, the bulk susceptibility of the resulting suspension can be made to match that of water. In this case, there will be no susceptibility artifact in a gradient echo image (FIG. 3). However, the favorable relaxation properties which make these suspensions good negative contrast agents are retained (FIG. 4).

The combination of diamagnetic $BaSO_4$ and SPIO in proper proportions results in a susceptibility-matched suspension which produces no artifacts in gradient echo images, yet retains a short $T_2$ which is useful in producing negative contrast. This mixture is useful as an improved oral negative contrast agent for use in gastrointestinal MRI.

TABLE 1

| Sample[a] | Spin-Lattice Relaxation Times ($T_1$) and Rates ($R_1$) Measured at 2.0 Tesla | |
|---|---|---|
| | $T_1$ (s)[b] | $R_1$ (1/s)[b] |
| Fe100 | 1.17 ± 0.04 | 0.855 ± 0.033 |
| Ba75 | 2.43 ± 0.22 | 0.413 ± 0.036 |
| Fe25 | 2.32 ± 0.17 | 0.432 ± 0.032 |
| Sum (Ba75 + Fe25) | 1.18 ± 0.10 | 0.845 ± 0.068 |
| Fe25/Ba75 | 1.60 ± 0.08 | 0.626 ± 0.032 |

[a]All samples contain 2.5% w/v vehicle to keep particles in suspension.
[b]Values are means ± S.D.

We claim:

1. A contrast agent adapted for magnetic resonance imaging of a sample, said contrast agent comprising a suspension in a medium acceptable for magnetic resonance imaging of (a) particles of a contrast agent possessing paramagnetic characteristics and (b) particles of a contrast agent possessing diamagnetic characteristics, the relative amounts of (a) and (b) in said suspension such that the positive magnetic susceptibility of (a) substantially offsets the negative magnetic susceptibility of (b) and the resulting suspension has substantially zero magnetic susceptibility and, when employed in magnetic resonance imaging, results in the substantial elimination of imaging artifacts.

2. A contrast agent according to claim 14 wherein said paramagnetic particles possess positive magnetic susceptibility characteristics.

3. A contrast agent according to claim 14 wherein said diamagnetic particles possess negative magnetic susceptibility characteristics.

4. A contrast agent according to claim 14 wherein said paramagnetic contrast agent particles are iron oxide.

5. A contrast agent according to claim 14 wherein said diamagnetic contrast agent particles are barium sulfate.

6. A contrast agent according to claim 14 wherein said paramagnetic contrast agent particles are iron oxide and said diamagnetic contrast agent particles are barium sulfate.

7. A contrast agent according to claim 14 for substantially artifact-free magnetic resonance imaging wherein said medium is also physiologically acceptable.

8. A method of imaging a sample which comprises introducing into said sample the contrast agent of claim 1 and generating an image thereof.

9. A method according to claim 8 for nuclear magnetic resonance imaging of a sample which comprises introducing into said sample the contrast agent of claim 14 and generating a substantially artifact-free NMR image thereof.

10. The contrast agent of claim 6 wherein said suspension comprises a mixture comprising an approximately 25% v/v suspension of particulate iron oxide in a suitable medium and approximately 75% v/v suspension of particulate barium sulfate in a suitable medium.

11. The contrast agent of claim 4 wherein said iron oxide particles are superparamagnetic iron oxide.

12. The contrast agent of claim 5 wherein said barium sulfate particles comprise a mixture of barytes and substantially pure barium sulfate.

* * * * *

UNITED STATES PATENT AND TRADEMARK OFFICE
CERTIFICATE OF CORRECTION

PATENT NO. : 5,323,780
DATED : June 28, 1994
INVENTOR(S) : Richard W. BRIGGS, ET AL          PAGE 1 OF 2

It is certified that error appears in the above-identified patent and that said Letters Patent is hereby corrected as shown below:

On the title page in column 1 under "[56] References Cited - U.S. PATENT DOCUMENTS" please include the following:

```
-- 4,731,239   3/1988   Gordon............... 424/9
   4,749,560   6/1988   Elgavish............. 424/9
   4,770,183   9/1988   Groman et al......... 128/654
   4,827,945   5/1989   Groman et al......... 128/653
   4,863,715   9/1989   Jacobsen et al....... 424/9
   4,951,675   8/1990   Groman et al......... 128/653
   5,055,288  10/1991   Lewis et al.......... 424/9
   5,069,216  12/1991   Groman et al......... 128/653.4 --
```

Please change the third entry under "[56] References Cited - U.S. PATENT DOCUMENTS" to read as follows:

-- 5,023,072   6/1991   Cheng ............... 424/9 --

Column 6, line 16 [claim 1, line 1]: delete "resonsance" and insert -- resonance --

Column 6, line 29 [claim 2, line 1]: delete "14" and insert -- 1 --

Column 6, line 32 [claim 3, line 1]: delete "14" and insert -- 1 --

Column 6, line 35 [claim 4, line 1]: delete "14" and insert -- 1 --

UNITED STATES PATENT AND TRADEMARK OFFICE
CERTIFICATE OF CORRECTION

PATENT NO. : 5,323,780
DATED : June 28, 1994
INVENTOR(S) : Richard W. BRIGGS, ET AL It is certified that error appears in the above-identified patent and that said Letters Patent is hereby corrected as shown below:

Column 6, line 38 [claim 5, line 1]: delete "14" and insert -- 1 --

Column 6, line 41 [claim 6, line 1]: delete "14" and insert -- 1 --

Column 6, line 45 [claim 7, line 1]: delete "14" and insert -- 1 --

Column 6, line 54 [claim 9, line 4]: delete "14" and insert -- 1 --

Signed and Sealed this

Eleventh Day of October, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,323,780
DATED : June 28, 1994
INVENTOR(S) : Richard W. BRIGGS, ET AL It is certified that error appears in the above-identified patent and that said Letters Patent is hereby corrected as shown below:

On the title page, column 2, line 2 of the Abstract: after "imaging" insert -- of --

In column 1, line 19: delete "generate" and substitute -- generated --

In column 2, line 60: after "imaging" insert -- of --

Signed and Sealed this

Fourteenth Day of February, 1995

Attest:

BRUCE LEHMAN

*Attesting Officer*     *Commissioner of Patents and Trademarks*